US00PP20629P3

(12) United States Plant Patent
Roose et al.

(10) Patent No.: US PP20,629 P3
(45) Date of Patent: Jan. 5, 2010

(54) **MALE *ASPARAGUS* HYBRID 'M256'**

(50) Latin Name: *Asparagus officinalis*
Varietal Denomination: M256

(75) Inventors: Mikeal Roose, Riverside, CA (US); Neil K. Stone, Temecula, CA (US); Laverne F. Lippert, Anacortes, WA (US); Janice M. Gish, legal representative, Anacortes, WA (US)

(73) Assignee: The Regents of the University of California, Oakland, CA (US)

( * ) Notice: Subject to any disclaimer, the term of this patent is extended or adjusted under 35 U.S.C. 154(b) by 237 days.

(21) Appl. No.: 11/732,506

(22) Filed: Apr. 2, 2007

(65) Prior Publication Data

US 2008/0244796 P1 Oct. 2, 2008

(51) Int. Cl.
*A01H 5/00* (2006.01)

(52) U.S. Cl. ..... Plt./260

(58) Field of Classification Search ..... Plt./260
See application file for complete search history.

*Primary Examiner*—Annette H Para
(74) *Attorney, Agent, or Firm*—Townsend and Townsend and Crew LLP

(57) ABSTRACT

This invention relates to a new and distinctive male *asparagus* hybrid called 'M256'. 'M256' has the ability to confer desirable traits on its progeny, such as early spear emergence, and produces offspring that have a higher proportion of marketable spears.

2 Drawing Sheets

Latin name of the genus and species: *Asparagus officinalis*.

Variety denomination: The variety denomination is 'M256'.

BACKGROUND OF THE INVENTION

*Asparagus* is a dioecious species with individual plants being either male or female. *Asparagus* cultivars that have been most commonly used for fresh market green *asparagus* in the major growing regions of California include, Atlas, Grande, Ida Lea, and UC157. These cultivars are all produced from crossing a genetically unique male clone with a genetically unique female clone to produce F1 seed.

BRIEF SUMMARY OF THE INVENTION

'M256' is a new and distinct male *asparagus* hybrid that is used to produce *asparagus* cultivars that have commercially desirable traits. 'M256' can be distinguished from the closest varieties known to the inventor by its ability to produce offspring that have a higher proportion of marketable spears with tightly appressed bracts, and a significantly higher total yield when yields are added over several years. The variety is further distinguished by its ability confer early spear emergence to its progeny.

DETAILED DESCRIPTION OF THE INVENTION

Pedigree 'M256' was selected as a single plant in 1982 from the hybrid 'Ida Lea'. Ida Lea is a cultivar consisting of the F1 progeny of a cross between *asparagus* cultivars F189 (U.S. Plant Pat. No. PP5,317) and M138 (U.S. Plant Pat. No. PP5,316). From this F1 population, named "Ida Lea", a single male plant, M256 was selected. 'F189' (unpatented) is from a cross between 'F111' (unpatented) and M.O.P. (Male Open Pollinated). 'F111' a single plant selection from 'UC66' (unpatented). 'M138' is from a cross between 'F120' (unpatented) and M.O.P. 'F120' is a single plant selection from 'UC309' (unpatented).

'M256' was selected as a single plant and propagated by tissue culture. Propagation by tissue culture was performed on the campus fo the University of California, Riverside, in Riverside, Calif., U.S.A. In 1987 'M256' was planted into a female block in Field 6AS. 'M256' conferred early spear emergence to its progeny. In 1989 'M256' *asparagus* crowns were transferred to a female holding block sufficiently isolated from other *asparagus* on the field station to produce hybrid seed of the genetic purity required for use in a field trial to evaluate 'M256' offspring. In 1990 the seed resulting from pollination of many of the females in the holding block with 'M256' was used to plant seedlings in a new trial to evaluate 'M256' offspring.

'M256' can be distinguished from its parent cultivars and other similar cultivars by the ability to confer desirabile traits on its offspring when crossed with a female *asparagus*. Specifically, 'M256' produces offspring that have a higher proportion of spears with tightly appressed bracts. 'M256' also has the ability confer early spear emergence to its progeny.

Cultivation 'M256' can be clonally propagated by crown division. The distinguishing characteristics of 'M256' are stable and reproduce true to type in successive generations. 'M256' is usually grown in isolated plantings of clonally propagated plants along with a female clone to produce F1 seeds. Recommended cultural practices for 'M256' are similar to those of other *asparagus* plantings for seed production. Plantings can be established using 8-week old seedling transplants or 1-year-old crowns. Performance can be good on soils with low (Riverside, Calif.) or high (Delta regions of California) organic content. Rust and *asparagus* aphid should be controlled with spray regimes. Periodic genetic tests of parent clones are typically conducted to verify genetic purity, or identify any problems that may arise. Some ways of maintaining genetic purity include hand harvesting of stalks with mature seed, planting clones in rows of all males and all females so as to be able to identify any volunteers of the opposite sex within the row, practicing no-till farming, applying pre-emergent chemicals to inhibit seed germination, periodic inspections and seedling removal by hand.

Plant Characteristics

Figure 1:
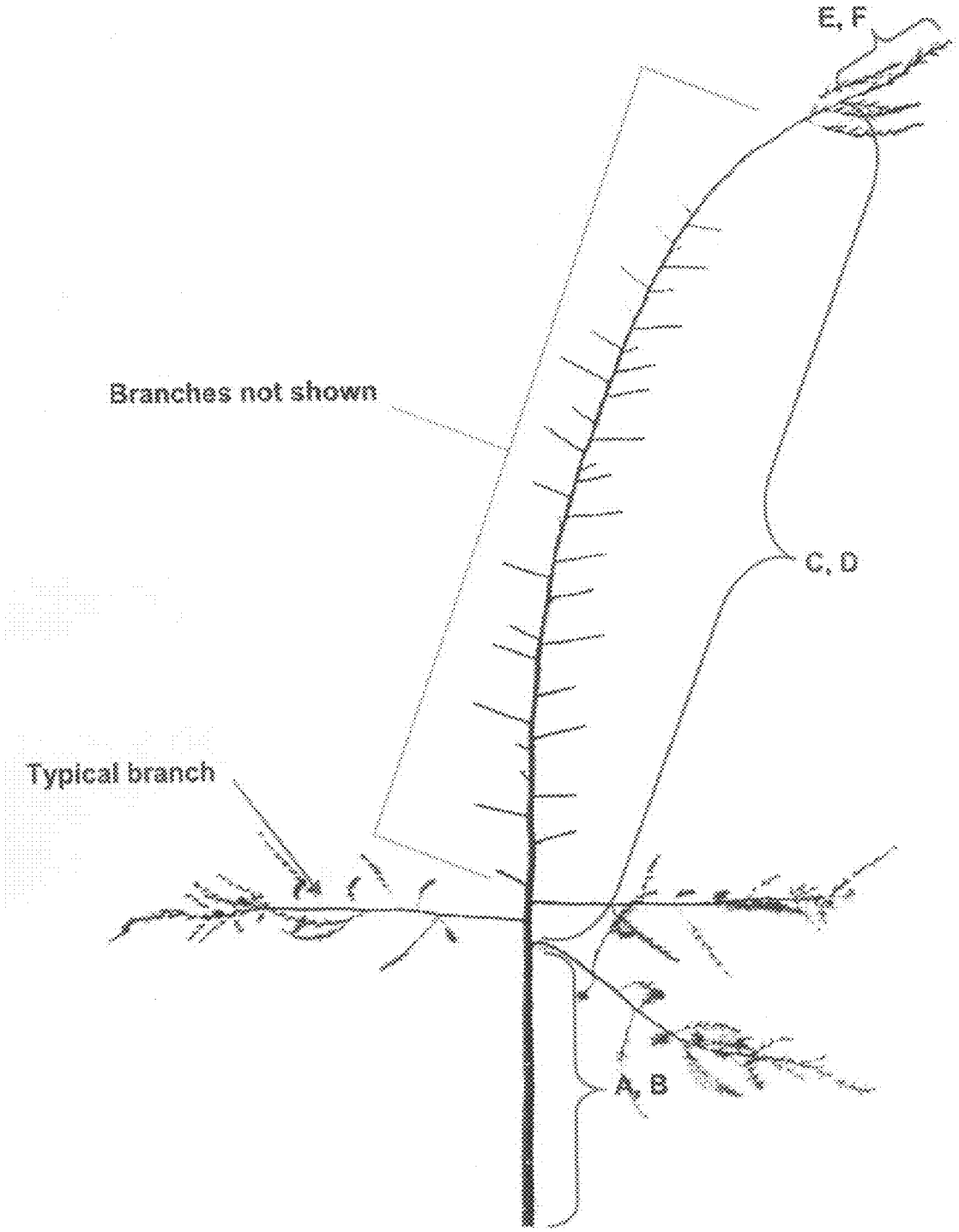
FIG. 1 provides an illustration of a typical stalk from an *asparagus* plant. The Figure illustrates the relative positions on the plant and the source of the data presented below. References are made with the use of brackets and letters, the same letters which are also listed in parentheses under the stalk data.

The attached photograph, FIG. 1, illustrates the relative positions on the plant and the source of the data presented below. References are made with the use of brackets and letters, the same letters which are also listed in parentheses under the stalk data.

Figure 2:
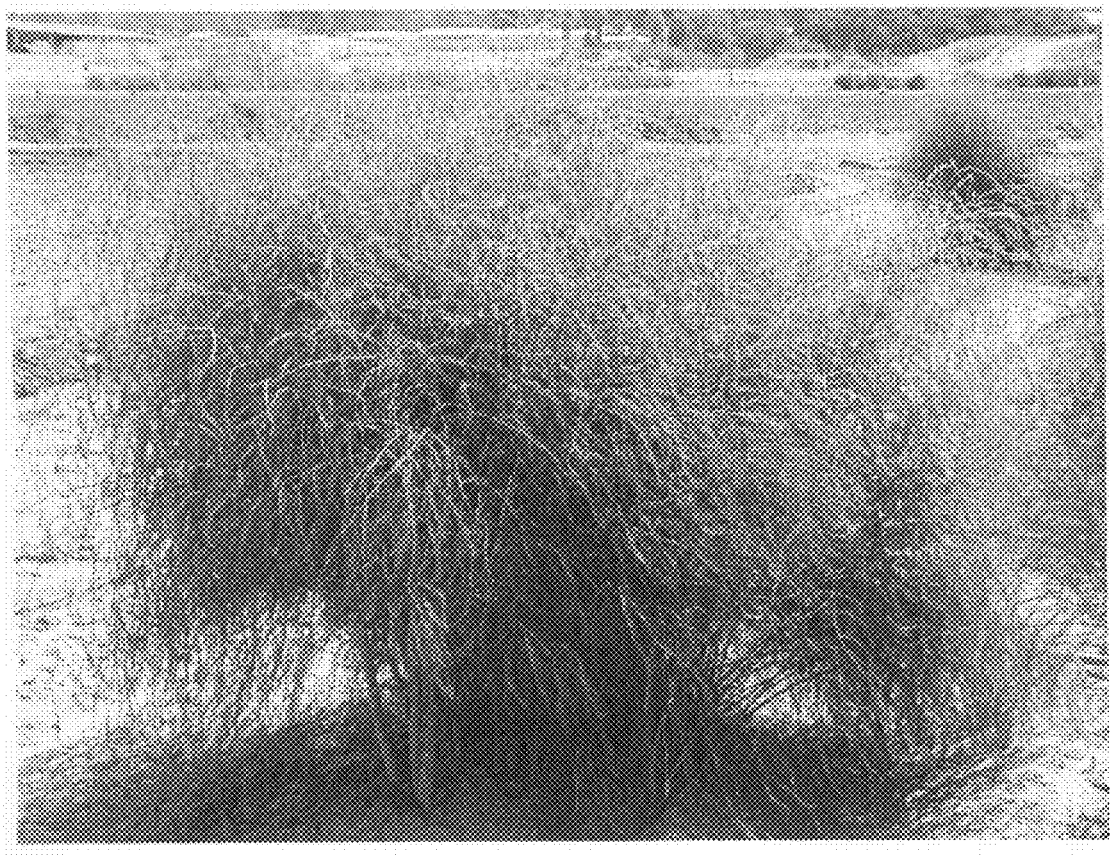
FIG. 2 shows typical foliage of'M256'. The photograph depicts a 10 year-old plant of 'M256' growing in Riverside, Calif.

Typical foliage of M256 is shown in FIG. 2.

The following data were obtained from the longest stalk and are the mean value of measurements on five separate plants unless otherwise indicated. The plants measured were genetically identical. All measured plants were planted from crowns (vegetative propagules) in October 1996. These plants were planted in Field 15E on the University of California, Riverside Citrus Experiment Station (Latitude 33°57'44.77" N, Longitude 117°20'16.27" W, elevation 1000 ft). The soil type is a Hanford coarse sandy loam. Plants were spaced five feet apart within and five feet apart between rows. The plants were irrigated with drip irrigation for a 24 hour period once every two weeks. Measurements were made in July, 2005, 8 years and 9 months from the planting.

The colors presented below refer to colors in The Royal Horticultural Society Colour Chart and are the most common colors observed among the plants measured.

Stalk data:

*Number of nodes below the first branch* (*A*).—27.6.

*Number of cm from crown to the first branch* (*B*).—57.2.

*Number of branches* (*C*).—55.8.

*Number of cm between first and last branch* (*D*).—116.4.

*Internode length in cm between branches* (*D*/(*C*-1)).—2.132.

*Number of cladophyll nodes beyond the last branch* (*E*).—47.6.

*Number of cm beyond the last branch* (*F*).—24.1.

*Internode length in cm beyond the last branch*(*F*/(*E*-1)).—0.52.

*Largest stalk diameter in mm.*—16.42.

*Mean diameter of three largest stalks in mm.*—14.72.

*Number of stalks.*—60.6.

*Stalk vigor index* (*stalk number*)(*mean diameter*)$^2$.—13402.71.

*Mature stalk color, bloom removed.*—144A.

Flower data: Tepals occur in two whorls of three, with no evident differences between inner and outer whorls.

*Tepal colors.*—Lower (abaxial) base: greyed orange 177D. lower (abaxial) tip: green yellow 1D. lower (abaxial) midrib: yellow green 146C. lower (abaxial) margins: green yellow 1D. upper (adaxial) base: green yellow 1D. upper (adaxial) tip: green yellow 1D. upper (adaxial) midrib: yellow green 146C. upper (adaxial) margins: green yellow 1D.

*Flower length in mm.*—5.7.

*Flower width at midpoint in mm.*—2.58.

*Flowers occur singly, borne two from each axil of a lateral branch.*

*Male flowers outer tepal length.*—5.71 mm.

*Male flowers outer tepal width.*—1.89 mm.

*Inner tepal length.*—5.72 mm.

*Inner tepal width.*—2.43 mm in width.

*Midrib of outer tepals, width.*—Average 0.65 mm.

*Midrib inner tepals, width.*—Averages 0.57 mm.

*Flower stalk.*—Peduncles: Length: 4.13 mm average. Diameter: 0.41 mm. Color: grey-brown 199A. Pedicels: Length: average 6.2 mm average. Diameter: 0.55 mm. Color: grey-brown 199A.

*Male reproductive organs of the male flowers.*—Rudimentary ovary: length, 1.48 mm; width: 1.16 mm. rudimentary style: length, averaging 0.18 mm long. Filament length: average 2.1 mm. Filament width: average 0.30 mm. Anther length: average 1.22 mm. Anther width: average 0.46 mm. Color of anthers before dehiscence: yellow-orange 22A. Pollen color: orange 25B.

Cladophyll data:

*Number per node.*—3.3.

*Length in mm.*—13.96.

*Width in mm.*—0.27.

*Color.*—Yellow-green (144A).

*Cladophylls are terete in cross section for both the tip and base, averaging* 15.1 *mm long and* 0.43 *mm in diameter.*

True leaves: Not present in *Asparagus officinalis*.

What is claimed is:

1. A new and distinct male *asparagus* hybrid plant having the characteristics essentially as described and illustrated herein.

* * * * *